(12) United States Patent
Granda (10) Patent No.: US 12,234,496 B1
(45) Date of Patent: Feb. 25, 2025

(54) SYSTEMS AND PROCESSES FOR OBTAINING NATURAL PRESERVATIVES AND NUTRITIONAL SUPPLEMENTS

(71) Applicant: BioVeritas, LLC, Bryan, TX (US)

(72) Inventor: Cesar Granda, College Station, TX (US)

(73) Assignee: BioVeritas, LLC, Bryan, TX (US)

( * ) Notice: Subject to any disclaimer, the term of this patent is extended or adjusted under 35 U.S.C. 154(b) by 201 days.

(21) Appl. No.: 17/383,373

(22) Filed: Jul. 22, 2021

Related U.S. Application Data (60) Provisional application No. 63/055,132, filed on Jul. 22, 2020.

(51) Int. Cl.

| | |
|---|---|
| C12P 7/44 | (2006.01) |
| A23K 20/158 | (2016.01) |
| A23L 3/3517 | (2006.01) |
| A23L 33/12 | (2016.01) |
| C12N 1/20 | (2006.01) |
| C12P 7/52 | (2006.01) |

(52) U.S. Cl.
CPC .............. *C12P 7/44* (2013.01); *A23K 20/158* (2016.05); *A23L 3/3517* (2013.01); *A23L 33/12* (2016.08); *C12N 1/20* (2013.01); *C12P 7/52* (2013.01); *A23V 2002/00* (2013.01)

(58) Field of Classification Search
CPC . C12P 7/44; C12P 7/52; A23K 20/158; A23L 3/3517; A23L 33/12; C12N 1/20; A23V 2002/00
See application file for complete search history.

(56) References Cited

U.S. PATENT DOCUMENTS

| | | | |
|---|---|---|---|
| 2,154,449 A | | 4/1939 | Hoffman et al. |
| 2,466,663 A | | 4/1949 | Russ et al. |
| 5,962,307 A | * | 10/1999 | Holtzapple ............ C12M 21/04 |
| | | | 435/813 |
| 6,132,786 A | | 10/2000 | Poulos et al. |
| 6,410,783 B1 | * | 6/2002 | Peterson ............... C07C 51/412 |
| | | | 562/405 |
| 8,232,440 B2 | | 7/2012 | Holtzapple et al. |
| 8,431,368 B2 | | 4/2013 | Hamelers et al. |
| 10,662,447 B2 | | 5/2020 | Ross et al. |
| 2012/0149076 A1 | | 6/2012 | Granda |
| 2013/0045299 A1 | | 2/2013 | Bright et al. |
| 2014/0037698 A1 | | 2/2014 | Pablos |
| 2014/0178951 A1 | * | 6/2014 | Ross ......................... C12P 7/40 |
| | | | 435/134 |
| 2019/0142800 A1 | | 5/2019 | Ghosh et al. |

FOREIGN PATENT DOCUMENTS

| | | | |
|---|---|---|---|
| WO | WO-01/97799 | 12/2001 | |
| WO | WO-2017/112841 | 6/2017 | |
| WO | WO-2019068642 A1 * | 4/2019 | ............ C12P 7/40 |

OTHER PUBLICATIONS

Alexandri, M. et al., "Downstream separation and purification of succinic acid from fermentation broths using spent sulphite liquor as feedstock", Separation and Purification Technology 209: 666-675 (Year: 2019).*
Saboe, P. et al., "In situ recovery of bio-based carboxylic acids", Green Chem 20: 1791-1804 (Year: 2018).*
Galfi et al., Feeding trial in pigs with a diet containing sodium n-butyrate, Acta Veterinaria Hungarica 38(1-2):3-17, Feb. 1990, 15 pages.
Guan et al., Efficacy of ionophores in cattle diets for mitigation of enteric methane, Journal of Animal Science, vol. 84, Issue 7, Jul. 2006, pp. 1896-1906, 11 pages.
Hanaki et al., Mechanism of Inhibition Caused by Long-Chain Fatty Acids in Anaerobic Digestion Process, Biotechnology and Bioengineering, vol. 23, 1591-1610, 1981, 20 pages.
Hristov et al., An inhibitor persistently decreased enteric methane emission from dairy cows with no negative effect on milk production, Proceeding of the National Academy of Sciences of the United States of America, vol. 112, No. 34, 10663-10668, Aug. 25, 2015, 6 pages.
Katoh et al., Effects of acetylcholine and short-chain fatty acids on acinar cells of the exocrine pancreas in sheep, The Journal of Physiology, vol. 356, Issue 1, Nov. 1, 1984, 11 pages.
Kucek et al., Conversion of l-lactate into n-caproate by a continuously fed reactor microbiome, Water Research, vol. 93, 163-171, Apr. 15, 2016, 37 pages.
Pearlin et al., Role of acidifiers in livestock nutrition and health: A review, Journal of Animal Physiology and Animal Nutrition, Jan. 8, 2020, 12 pages.
Sunkara et al., Butyrate Enhances Disease Resistance of Chickens by Inducing Antimicrobial Host Defense Peptide Gene Expression, PLoS One 6(11), e27225, Nov. 2011, 10 pages.
Thiel, The Effect of Methane Analogues on Methanogenesis in Anaerobic Digestion, Water Research, vol. 3, 215-223, 1969, 9 pages.

* cited by examiner

*Primary Examiner* — Anand U Desai
(74) *Attorney, Agent, or Firm* — FOLEY & LARDNER LLP (57) ABSTRACT

A process for producing products containing organic salts from biodegradable feedstocks includes fermenting biodegradable feedstock using natural consortia of microorganisms to produce a first product stream including carboxylic acid salts, suspended solids and water; removing suspended solids from the first product stream to produce a second product stream including carboxylic acid salts; concentrating the second product stream to produce a third product stream and water; and further drying the third product stream to remove water and produce a fourth product stream including dry carboxylic acid salts.

17 Claims, 2 Drawing Sheets

SYSTEMS AND PROCESSES FOR OBTAINING NATURAL PRESERVATIVES AND NUTRITIONAL SUPPLEMENTS

CROSS-REFERENCE TO RELATED APPLICATIONS

This application claims priority to U.S. Provisional Application 63/055,132, filed Jul. 22, 2020, incorporated in its entirety herein.

BACKGROUND

Field of the Disclosure

This disclosure pertains to methods for recovering salts of organic acids, namely short-chain fatty acids, which are acetic, propionic, isobutyric, butyric, isovaleric and valeric acids, medium-chain fatty acids, which are caproic, enanthic and caprylic acids, produced in buffered mixed-acid fermentation with naturally occurring microorganisms, which can be then used as natural preservatives for food and feed and as nutritional supplements for human and animal consumption. Embodiments of the disclosure also pertain to integrating such aspects to produce such natural preservatives and nutritional supplements.

Background of the Disclosure

Throughout this specification, the term "volatile fatty acids" or its abbreviation "VFAs" are used interchangeably with "carboxylic acids" and with "organic acids" to denote the organic acids of carboxylic type produced in mixed-acid fermentation, also known as anaerobic digestion. In mixed-acid fermentation or anaerobic digestion, naturally occurring consortia of anaerobic microorganisms produce VFAs, such as, but not limited to, acetic (C2, also known as ethanoic), propionic (C3, also known as propanoic), isobutyric (C4, also known as 2-methylpropanoic), butyric (C4, also known as butanoic), isovaleric (C5, also known as 3-methylbutanoic), valeric (C5, also known as pentanoic), caproic (C6, also known as hexanoic), enanthic (C7, also known as hexanoic) and caprylic (C8, also known as octanoic) acids. C2 through C5 acids are sometimes known as short-chain fatty acids, while C6 through C8 acids are sometimes known as medium-chain fatty acids. Smaller amounts of higher acids, such as pelargonic (also known as nonanoic), capric (also known as decanoic) and undecylic (also known as undecanoic) acids have also been detected in analyses. The acids are neutralized in the mixed-acid fermentation to control pH thus ending up with the salts of the acids referred to, throughout this specification, interchangeably as "organic salts", "mixed-acid salts", "VFA salts", "carboxylic acid salts", "carboxylate salts", "short- and medium-chain fatty acid salts", or, at times, generically as "salts".

Throughout this specification, the term "natural consortia of microorganisms" is used to denote a consortium of microorganisms or the mixture of several consortia of microorganisms in one or more vessels, or the use of two or more consortia of microorganisms in, whose original inocula are obtained from natural locations where organic acids are naturally produced, such as, but not limited to, the rumen of cattle, saltwater marshes, methanogenic anaerobic digesters, and combinations thereof or even no inoculum might be used and the natural microorganisms present in the feedstock are allowed to naturally develop. The word "natural" denotes that these microorganisms occur naturally and have not been isolated or genetically modified, manipulated or engineered.

The use of organic acids, specifically volatile fatty acids (VFAs), as antibacterial, antifungal, antimycotic and, in general, as antimicrobial agents is well known. Earliest patents in mold inhibition in food employing organic acids date to early $20^{th}$ century (U.S. Pat. No. 2,154,449), when the now common use of propionic acid and its salts thereof was introduced.

Ample use of propionic acid salts is found in the food and feed industries as an anti-molding agent. Propionic acid is commonly produced from petroleum and then neutralized to form the salts with alkaline buffering agents such as ammonium, calcium, potassium, and sodium hydroxide or carbonate. Such preservative is considered a chemical, which, given the drive for natural, clean-label products in recent years, is becoming a less desirable product. The drive for natural and clean-label preservatives has moved many players in the industry to employ fermentation, typically using isolated cultures, such as Propionibacterium (U.S. Pat. No. 6,132,786) to produce an organic-acid rich product, which can be employed instead of other chemical preservatives, such as propionic acid salts, but also sodium benzoate and potassium sorbate. Many products exist in the market where natural feedstocks such as whey, wheat flour, and free sugars such as dextrose are used to produce a cultured product that is recognized as natural and clean label. Other alternatives may also employ other buffered natural acids, such as lactic acid, acetic acid (vinegar) and others to produce a natural preservative (U.S. patent application Ser. No. 13/584,200).

The above products are recognized preservatives, which are added to food and feed for preservation against molds, bacteria, and yeast. However, the antimicrobial properties of organic acids have also been found beneficial if applied directly to human and animals. Early patents where salts of medium-chain fatty acids, such as caprylic acid, are used as a fungicide being applied directly to the skin or ingested date back to the first half of the $20^{th}$ century (U.S. Pat. No. 2,466,663). Other recent uses of medium-chain fatty acids, such as caprylic, as antifungals to be applied to the skin have also been proposed (U.S. patent application Ser. No. 16/309, 751). A lot of interest has also been directed to short- and medium-chain fatty acids due to their antimicrobial properties as nutritional supplements towards improving human and animal gastrointestinal tract health (International Patent Appl No. PCT/EP01/06973). Drives for antibiotic bans in animal health, for instance, have caused demand for these short- and medium-chain fatty acids as nutritional supplements to increase (Pearlin B. V. et al., J Anim Physiol Nutr 104: 558-569, 2020). Along with the antimicrobial effect, short-chain fatty acids, with most of the research at the moment being centered around butyric acid, have also shown other benefits in other areas such as increase in immune response and disease resistance (Sunkara L. T. et al., PLoS One 6(11): e27225, 2011), increases in pancreatic fluid secretion (Katoh K. and Tsuda T., J Physiol 356: 479-489, 1984) and improvement in adsorption of electrolytes decreasing incidence of diarrhea (Galfi P. and Bokori J., Acta Vet Hung 38(1-2):3-17, 1990). With the proper protection, such as encapsulation, coating or conversion to glycerides, these short-chain fatty acids can reach the hindgut, namely the distal sections of the gastrointestinal tract, the cecum and colon, where these acids act to control the presence of pathogenic bacteria and at the same time stimulate the growth of good bacteria and improved development of intestinal epithelium, which provide bring their own set of benefits, such as immuno-stimulation and better food absorption (U.S. patent application Ser. No. 13/980, 469). As with conventional food and feed preservatives, when these organic acids are used as food and feed supplements to improve gastrointestinal health, they are typically obtained from petroleum-based sources. Butyric acid, for instance, is mainly produced using hydroformylation (OXO process) of propylene derived from natural gas to form butyraldehyde, followed by its oxidation. As a result, they cannot be considered natural. There has been interest in producing these acids through fermentation of carbohydrates alone or accompanied by the fermentation of other products such as protein (International Appl. No. PCT/US20 16/068 194). Such processes bring to the table the organic acids produced in the fermentation, microbial protein, and the pro-biotic effect of such microorganisms. However, although natural, such process does not allow for pure organic acids or salts, and as a result, it offers little flexibility in the application to food or feed formulations and makes it difficult to apply protections as described previously to reach the hindgut to offer their aforementioned benefits.

Mixed-acid fermentation employing a consortium of naturally occurring microorganisms is a one the most robust, ubiquitous, and ancient fermentation processes which produces organic acids, which are carboxylic in kind, namely short- and medium-chain fatty acids, also known as volatile fatty acids (VFAs). Such organic acids, if properly processed and recovered, may be employed as natural preservatives and nutritional supplements with similar properties and benefits as the petroleum-based versions of these acids mentioned. Mixed-acid fermentations occur naturally in the rumen of ruminant animals like cows and goats and in termite guts and commercially can be found in anaerobic digesters in methanogenic biogas production, (although in this case, the acids once produced are converted to methane and carbon dioxide, which would be undesirable for our purposes in this invention). Mixed-acid fermentation offers a lot of flexibility as to the feedstocks that can be employed given that the natural consortium is able to degrade most biodegradable materials. Such flexibility is important to be able to offer products with characteristics that are gaining traction among consumers such as GMO-free, gluten-free, organic, clean-label and, of course, natural. In addition, regardless of the feedstock used, the fermentation always produces the same aforementioned products, i.e., short- (acetic, propionic, isobutyric, butyric, isovaleric and valeric acids) and medium-chain fatty acids (caproic, heptanoic and caprylic acids), albeit in different concentrations depending of the feedstock and operating conditions. With knowledge of how the different acids profiles and feedstock formulations and operating conditions such as temperature, pH and residence time, correlate with each other, it is possible to have some control of the profile of the short- and medium-chain fatty acid generated. As pH is adjusted by adding a buffering agent, the corresponding salts of the acids are formed.

Further processing of the generated effluent or fermentation broth which contains the salts of the short- and medium-chain fatty acids from mixed-acid fermentation may take many forms, such as, but not limited to, processes such as those described in U.S. Pat. No. 10,662,447, which is incorporated here by reference in its entirety for all purposes. Such processing, as described in U.S. Pat. No. 10,662,447, may consist of clean-up of the effluent or fermentation broth, which may include, but it is not limited to liquid/solid separation and clarification with membranes, prior to concentration, crystallization and drying, to generate a product. It may also include, in addition to the clean-up, the recovery of the short- and medium-chain fatty acids from their salts, which may then be further purified or fractionated by distillation. These pure, either individual or mixed acids, may be combined as desired to obtain a preferred profile of acids and again may be converted into salts, by neutralizing the acids with a buffering agent, such as but not limited to sodium, potassium, ammonium, calcium or magnesium hydroxide or carbonates or combinations thereof. The resulting salts may then be subjected to concentration, crystallization and drying to generate a product.

SUMMARY

Embodiments of the disclosure pertain to a process for producing products containing organic salts from biodegradable feedstocks that may include fermenting biodegradable feedstock using natural consortia of microorganisms to produce a first product stream comprising carboxylic acid salts, suspended solids and water; removing suspended solids from the first product stream to produce a second product stream including carboxylic acid salts; concentrating said second product stream to produce a third product stream and water; and further drying the third product stream to remove water and produce a fourth product stream that includes dry carboxylic acid salts.

Fermenting biodegradable feedstock using natural consortia of microorganisms includes anaerobic fermentation with a mixed culture of natural microorganisms in a fermentation vessel or systems of vessels. Fermenting biodegradable feedstock occurs at a pH between about 5 and about 8, but more often a pH between about 6 and about 7 controlled by adding a buffering agent. In addition, the fermentation occurs at a temperature between about 30° C. and about 60° C., but more often between about 35° C. and about 45° C. Methane production in the fermentation is inhibited.

Removing suspended solids from the first product stream includes using at least one of the following: filtration, centrifugation, membrane filtration, high-speed centrifugation, and combinations thereof. Further removing suspended solids from the first product stream after filtration or centrifugation includes further clarification using membrane filtration, high-speed centrifugation, or combinations thereof.

Concentrating may include using reverse osmosis or evaporation, or both in that order. The water produced by concentrating the second product stream is recycled to the fermentation. Concentration may cause crystallization of the carboxylic acid salts. During crystallization, the crystallized carboxylic acids salts are recovered from the solution as they form thus causing fractionation of the carboxylic acid salts and thus producing several fractions of the carboxylic acid salts. Some fractions of carboxylic acid salts might consist mostly of medium-chain fatty acid salts (C6-C9 salts), other fractions might be formed mostly of short-chain fatty acid salts (C2-C5 salts), yet other fractions may be controlled to consist mostly of individual carboxylic acid salts (mostly acetate, propionate, isobutyrate, butyrate, isovalerate, valerate, caproate, heptoate, caprylate or pelargonate). A fraction of carboxylic acid salts might be recycled to the fermenting step to effect elongation and increase medium-chain fatty acid salts production.

Drying may include using a drum dryer, a flash dryer, a spray dryer, or combinations thereof. The resulting dry carboxylic acid salts may be further ground or milled to produce a fine powder. The dry carboxylic acids salts may be packaged directly from the dryers or after grinding or milling to produce a final product to be marketed as a natural preservative or as a nutritional supplement for animal feed or human consumption or both.

The salts produced will depend on the buffering agent used to control pH in the fermentation, which could be one of the following: sodium hydroxide, potassium hydroxide, calcium hydroxide, magnesium hydroxide, sodium carbonate, potassium carbonate, calcium carbonate, magnesium carbonate, calcium oxide, magnesium oxide, and combinations thereof.

Another embodiment of the disclosure pertains to a process for producing products containing organic salts from biodegradable feedstocks comprising: fermenting biodegradable feedstock using natural consortia of microorganisms to produce a first product stream that includes carboxylic acid salts, suspended solids and water; removing suspended solids from the first product stream to produce a second product stream including carboxylic acid salts; concentrating said second product stream to produce a third product stream and water; acidifying, extracting and recovering acids from the third product stream to produce a fourth product stream consisting of carboxylic acids; purifying the fourth product stream to produce a fifth product stream that includes pure carboxylic acids; and neutralizing the fifth product stream to produce a sixth product stream comprising pure carboxylic acids salts.

Further the pure carboxylic acid salts produced may be concentrated and dried or simply dried as necessary to remove water and produce a seventh product stream, which includes pure dry carboxylic acids salts.

In this embodiment as in the previous one, fermenting biodegradable feedstock using natural consortia of microorganisms also includes anaerobic fermentation with a mixed culture of natural microorganisms in a fermentation vessel or systems of vessels. This fermentation occurs at a pH between about 5 and about 8, but preferably between about 6 and about 7, which is controlled by adding a buffering agent. The fermentation temperature may range between about 30° C. and about 60° C., but more preferably between about 35° C. and about 45° C. As in the previous embodiment, methane production during fermentation is inhibited.

The removal of suspended solids from the effluent from the fermentation includes using at least one of the following: filtration, centrifugation, membrane filtration, high-speed centrifugation, and combinations thereof. Further removing suspended solids from the fermentation product after filtration or centrifugation includes further clarification using a membrane filtration, high-speed centrifugation, or both thus producing a second product.

Concentrating the second product stream may include reverse osmosis or evaporation, or both in that order. The water produced by concentrating the second product stream is recycled to the fermenting step.

The concentrated product then undergoes acidification and extraction, which can include liquid-liquid extraction using high-pressure carbon dioxide as the acidification agent and extractant and recovery may include distillation to recover and separate the extractant and produce the fourth product stream comprising carboxylic acids. At least a portion of the raffinate produced during acidification and extraction is recycled to the fermenting step as a buffering agent and another portion is purged to avoid accumulation of minerals.

Purifying the carboxylic acids includes distilling the acids to remove impurities. However, distillation is also used to separate the pure carboxylic acids to fractionate them and thus produce a fifth product stream, which includes fractions of pure carboxylic acids. Some fractions of carboxylic acids might consist mostly of medium-chain fatty acids (C6-C9 acids), other fractions might be formed mostly of short-chain fatty acids (C2-C5 acids), yet other fractions may be controlled to consist mostly of individual carboxylic acids (mostly acetic, propionic, isobutyric, butyric, isovaleric, valeric, caproic, enanthic, caprylic or pelargonic acids).

Neutralizing may include adding a buffering agent chosen from at least one of the following: sodium hydroxide, potassium hydroxide, calcium hydroxide, magnesium hydroxide, sodium carbonate, potassium carbonate, calcium carbonate, magnesium carbonate, calcium oxide, magnesium oxide, and combinations thereof. Concentrating may cause crystallization of the pure carboxylic acid salts if the salts are adequate (e.g., calcium).

The resulting pure carboxylic acid salts may then be dried using at least one of the following: drum dryer, a flash dryer, a spray dryer, and combinations thereof. If necessary, the pure dry carboxylic acid may be further ground or milled to produce fine powder of the pure dry carboxylic acid salts. The pure dry carboxylic acids salts may be packaged directly from the dryers or after grinding or milling to produce a final product to be marketed as a natural preservative or as a nutritional supplement for animal feed or human consumption or both.

BRIEF DESCRIPTION OF THE DRAWINGS

For a more detailed description of the present invention, reference will now be made to the accompanying drawings, wherein.

DETAILED DESCRIPTION

Herein disclosed are novel systems, and methods that pertain to converting different organic feedstocks or biomass into mixed-acid salts through buffered mixed-acid fermentation and the subsequent processing of the effluent from such buffered mixed-acid fermentation to produce mixed-acid salts products, which may be use as natural preservatives and nutritional supplements.

It should be understood that, although example implementations of embodiments of the disclosure are described herein, the systems, methods, and processes of this disclosure may be implemented using any number of techniques, whether currently known or not. The present disclosure should in no way be limited to the example implementations, drawings, and techniques illustrated below. Additionally, the drawings are not necessarily drawn to scale and may not illustrate obvious pieces of equipment such as valves, pumps and instrumentation. One of ordinary skill in the art would readily understand the difference between a general process block flow diagram (BFD) as compared to the intricate and detailed aspects involved with an actual process. BFD(s) are described in general detail for brevity.

It is also noted, and as would be apparent to one of skill in the art, "process streams" described herein need not be clean cut or pure. When referring to particular product streams herein, it should be understood that, although the primary product(s) may be described, other products may exist in the product stream. Thus, there may be quantities of the other compounds in such streams and/or other impurities. When the qualifier "pure" is used, it should be understood to denote that the stream or substance it is qualifying is pure relative to the products intended to be produced in this specification and it does not mean that the stream or substance is completely pure or free of trace impurities, which might be critical for other applications.

When referring to any particular product streams herein, it should be understood that, although the primary product(s) may be described, other products may exist in the product stream. For example, if the fractionation process is said to be able to separate the carboxylic acids into a short-chain fatty acid fraction (Acetic, C2 through valeric, C5 acids), the bulk of the short-chain fatty acid fraction might comprise C2 through C5 acids, but this fraction may also contain, in addition to possibly some water (moisture), small quantities of medium-chain fatty acids (C6 and above) and other trace impurities.

Embodiments of the disclosure are often described in a stepwise manner (e.g., describing process flow step-by-step), but the disclosure should in no manner be limited. That is, one of skill in the art would easily grasp and understand the continuous operation that accommodates embodiments described, discussed, and illustrated. Although flow streams or products are often described as 'sent' from one location to another, the disclosure encompasses use of any and all aspects of fluid/product handling and transport (e.g., pumps, piping, vessels, etc.) that are well within the grasp of a skilled artisan. Finally, although any process stream may be shown as directed to a particular destination (e.g., unit operation, vessel, system, etc.), the destination and handling of the process stream is not limited to such a depiction. Thus, a process stream may be sent to a filter press, a membrane filtration unit, a reverse osmosis unit, an evaporator, combinations thereof, etc.

Embodiments disclosed herein provide recovering of salts of carboxylic acids, namely short-chain fatty acids and medium-chain fatty acids produced in buffered mixed-acid fermentation with natural consortia of microorganisms to produce natural preservatives for food and feed and as nutritional supplements for human and animal consumption.

Mixed-acid fermentation with natural consortia of microorganisms produces organic acids or, more precisely, carboxylic acids. This production of these mixed carboxylic acids uses naturally occurring anaerobic bacteria to convert any anaerobically biodegradable material or biomass into certain types of carboxylic acids known as volatile fatty acids (VFAs), namely acetic (C2), propionic (C3), butyric (C4), isobutyric (C4), valeric (C5) and isovaleric (C5) acid (C2 through C5 known as short-chain fatty acids) and caproic (C6), enanthic (C7), caprylic (C8) acids (C6 through C8 known as medium-chain fatty acids). Very small amount of pelargonic (C9), capric (C10) and undecylic (C11) acids have also been detected. These acids are neutralized with a buffering agent, such as sodium, potassium, ammonium, calcium, magnesium hydroxide or carbonate or combinations thereof, thus producing the organic salts of their corresponding acids. These organic salts may be further recovered and chemically converted into valuable chemicals and fuels; and they can also be first converted into the acids for purification and fractionation and then converted to chemicals and fuels; however, a more straight forward process would be to produce the salts as final product. Examples of processes that propose production of mixed carboxylic acids can be found in U.S. patent application Ser. No. 12/629,285, U.S. patent application Ser. No. 13/311,533 and U.S. patent application Ser. No. 12/745,226, incorporated by reference in entirety for all purposes.

Figure 1:
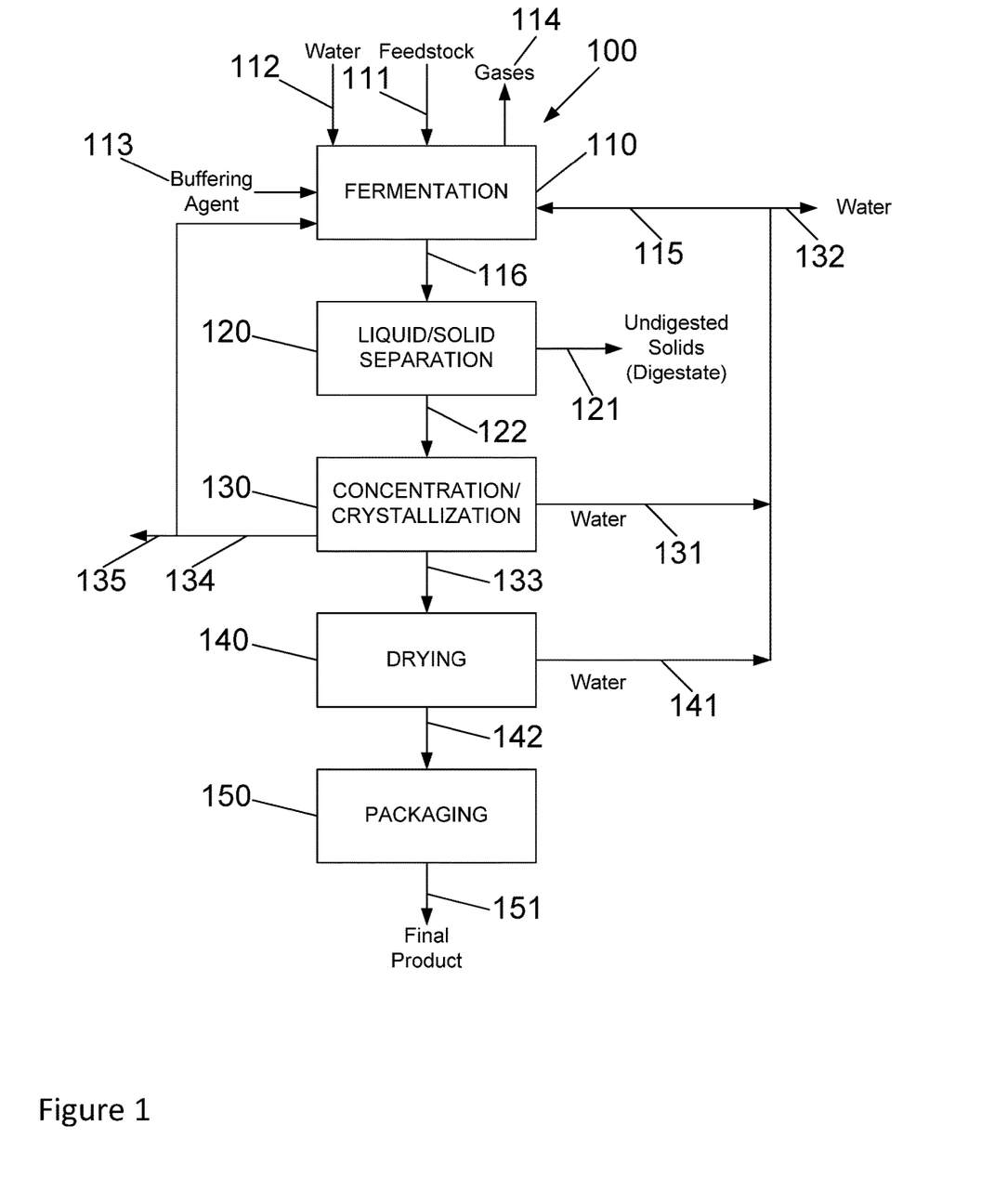
FIG. 1 shows a natural mixed-acid fermentation for producing short- and medium-chain fatty acid salts with further processing of the effluent containing these salts to obtain a natural dry product that may be sold as a natural preservative or as a nutritional supplement.

FIG. 1 shows Process 100 for the production of a dry product containing mixed carboxylic acid salts or VFA salts, which can be marketed as a natural preservative or nutritional supplement. Process 100 includes feeding into mixed-acid fermentation 110, where a mixed culture of naturally microorganisms produces mixed carboxylic acids or VFAs, a biodegradable feedstock 111, which gluten-free, free of allergens, organic, Kosher, Halal. The feedstock 111 may be prepared in various ways as necessary, such as, by grinding, or by sorting in some cases, prior to feeding to mixed-acid fermentation 110, and it might be fed along with water 112 (if necessary when the feedstock moisture content is low to attain a solids content of <20% but preferably <10%) with a large amount of the required water also being recycled from upstream unit operations 115. Temperature and pH, which tends to drop as the mixed acids are formed, are controlled. Temperature is typically kept at around 40° C., and may be controlled with, for example and not limited to, a sludge heater or heat exchanger, where hot water or steam if heating is needed or, at times, cooling water if cooling is needed, is passed through, while the fermentation contents are pumped through such heater or exchanger. On the other hand, pH is maintained at neutral (around 6.8 to 7) by adding a buffering agent 113. Lower temperatures (30° C. to 40° C.) and lower pH (5 to 7) have been employed to enhance the production of medium-chain fatty acids (caproic, heptanoic and caprylic acids, C6-C8, although small quantities of larger acids, C9-C11 can be also observed) and higher temperatures (40° C. to 60° C.) and higher pH (7 to 8) are known to enhance the production of short-chain fatty acids (C2-C4, acetic, propionic, isobutyric, butyric, valeric, isovaleric acids, C2-C5) with acetic acid (C2) being the main acid produced (>70%) at temperatures above 50° C. and pH above 7.2.

The neutral pH allows for more conversion of the feedstock into mixed carboxylic acids, and feedstock conversion drops as the pH deviates from about 6.8. As a result, if, for instance, a higher amount of medium-chain fatty acids are desired, a two-stage fermentation configuration may be employed, with the pH in the first stage being kept neutral to maximize conversion, whereas the pH in the $2^{nd}$ stage is kept at a lower pH (e.g., 6 to 6.5) to maximize elongation to the medium-chain fatty acids. Other ways to effect a change in the acid profile is to choose certain feedstocks or supplement the fermentation with certain feedstocks. For instance, the addition of ethanol or other reducing agents like lactate and even hydrogen, can enhance elongation towards medium-chain fatty acids (U.S. patent application Ser. No. 12/745,226, Kucek L. A. et al. Water Res. 93:163-171, 2016).

In addition to the mixed carboxylic acids, gases 114 are also produced in mixed-acid fermentation 110, which are mostly carbon dioxide and hydrogen. Methane may also be produced as a gas, but it should be avoided because this may indicate degradation of the acids as acetoclastic methanogens consume the acids to produce methane and carbon dioxide. Also, although methane is also produced from the autotrophic conversion of carbon dioxide and hydrogen, hydrogen is used by certain microorganisms for the elongation of short-chain fatty acids to medium-chain fatty acids, so if such elongation is desired, this is another reason to avoid methane production. As a result, methane production should be inhibited. Methane inhibition may be effected through different methods, such as controlling conditions, such as pH, or by the addition of certain methane inhibitors such as, but not limited to, long-chain fatty acids (Hanaki K. et al., Biotechnol Bioeng 23(7): 1591-1610, 1981), methane analogues (Thiel P., Water Res 3(3): 215-223, 1969), ionophores (Guan H. et al, J Anim Sci 84(7): 1896-1906, 2006) and others (Hristov A. et al, Proc Natl Acad Sci U.S.A. 112(34): 10663-10668, 2015), or by the combination of the methods and inhibitors thereof From the mixed-acid fermentation 110, an effluent 116 containing the produced organic salts of the mixed carboxylic acids (also known as carboxylate salts), water and any undigested solids, which would include the microorganisms, is generated. A liquid/solid separation step, 120, may be required to remove the undigested suspended solids or digestate 121, which comprises of the parts of the solid feedstock that are hard to digest or it may also comprise of microorganisms. Such liquid/solid separation process can be, but not limited to, a centrifuge (e.g., decanter centrifuge, basket centrifuge), a filtration system (e.g., plate-and-frame filter press, rotary-drum filter, belt filter press), a membrane filtration system (e.g., microfiltration, ultrafiltration, nanofiltration), high-speed centrifugation or combinations thereof. A flocculation chemical, a coagulation chemical or combination thereof may be added in this step as necessary for the proper functioning of the liquid/solid separation process, and filter aid (e.g., diatomaceous earth) may also be employed, as necessary. The resulting digestate 121 may be further washed to recover as much as the organic acid salts still present and then the wash water containing the recovered organic acid salts may be sent back to the fermentation 110. The digestate 121 may be disposed of or it may be sent to composting to be land applied. Yet part of the digestate 121 may be recycled to the fermentation 110 for further conversion. The filtrate effluent from the filtration or the supernatant effluent from the centrifugation may be further cleaned up or clarified to further remove suspended solids. Such cleaning or clarification may be important to improve the quality of the effluent. Such cleaning or clarification may be done using microfiltration, ultrafiltration, nanofiltration membranes or combinations thereof. Yet another method for removal of suspended solids to clean up and clarify the effluent may be high-speed centrifugation. The retentate from the membrane clarification containing the suspended solids or the centrifuged suspended solids from the high-speed centrifugation (above 10,000 RPM) may be recycled to the fermentation 110 for further conversion. The resulting permeate from the membrane clarification or the supernatant from the high-speed centrifugation 122 is then sent to concentration 130.

Concentration 130 has the objective of removing water 131 from the clarified effluent to increase the concentration of the organic salts. Such concentration may occur by reverse osmosis (RO) with membranes, by evaporation or by combinations thereof. Typically, RO is used first when the concentration is low followed by evaporation as the concentration gets to a point where the required RO pressure would be too large. This strategy of using RO followed by evaporation can minimize operating costs, nonetheless, in some embodiments both RO and evaporation may be employed alone. The evaporator can be of any type, such as, but not limited to, a simple evaporator, multiple-effect evaporator, mechanical vapor-recompression evaporator and thermocompression evaporator. pH may be increased in this step by adding alkali, for instance sodium, potassium, ammonium, calcium or magnesium hydroxide or carbonate or combinations thereof. The purpose of increasing the pH is avoiding the loss of the organic acids both during the RO step and the evaporation. In the RO step, undissociated acids may go through the membrane easier than salts, which surround themselves with water molecules. During the evaporation, on the other hand, making sure that all the acids are indeed in the salt form rather than undissociated is also important to avoid the acids from volatilizing. Typically, a pH above 8.5 is enough to avoid acid losses in RO and evaporation.

From RO, the permeate that goes through the membrane is very pure potable water. Also, the evaporators would produce as outputs the concentrated liquid 133 and the water removed would also be recovered as condensate. The water 131 obtained from this concentration step either in RO, evaporation or both may be recycled 115 to fermentation 110, or if the feedstock moisture content is high, then excess water 132 may be an output from the system. The water should be good quality either RO-quality or distilled water in the condensate from evaporation. Now, at high pH, ammonia, which, if not added as alkali or buffer, is also produced from the degradation of proteins in the mixed-acid fermentation 110, will be removed during RO but mostly during evaporation. Some of the ammonia will end up in the RO water, but a more significant amount will end up in the condensate from the evaporation. The ammonia will need to be removed to be able to outfall excess water 132. Even if the water is to be recycled 115 to fermentation 110, it also requires the removal of some ammonia to avoid ammonia accumulation. Ammonia removal can take place by many methods, such as, but not limited to, ion exchange, hollow fiber membranes under vacuum, and air or steam stripping. The removed ammonia may be recovered with sulfuric acid as liquid ammonium sulfate, which can be sold as fertilizer.

The concentrated broth obtained from the concentration step 130, could have some precipitation in the form of some minerals, such as phosphates and struvite, which fall out of solution due to the removal of ammonia and other electrolyte chemistry alterations occurring during concentration. It is optional, in some embodiments, to implement filtration, such as bag filters, filter presses, or even membrane microfiltration, ultrafiltration or nanofiltration to remove such precipitated minerals. The concentrated filtrate is then sent optionally to crystallization and then sent to drying 140 or the concentrated broth is sent directly to drying 140.

In some embodiments, crystallization occurs during concentration 130 when the salts fall or precipitate out of solution as further concentration takes place, which means water 131 continues to be removed during the crystallization process. Such phenomenon has been observed with calcium salts, for instance, where the salts of the medium-chain fatty acids (C6 through C8) precipitate first, followed by the short-chain fatty acid salts (C2 through C5). As the salts are precipitated, they may be filtered out or centrifuged out. Because each salt will precipitate when different concentrations are reached depending on their own water solubility at a given temperature (See Table 1, the solubilities of calcium carboxylic acid salts at 100° C.), and the crystallized carboxylic acid salts may be recovered as they form (e.g., through filtration or centrifugation), the crystallization process is able to selectively separate, up to a certain degree, the different carboxylic acid salts present, thus it may produce salt fractions with different carboxylic acid profiles. For instance, in some embodiments, a fraction of the salts may have a salt profile with a higher concentration of medium-chain fatty acid salts (C6 through C8) and another fraction with a higher concentration of short-chain fatty acid salts (C2 through C5), yet another embodiment might be directed to concentrate a particular salt (e.g., C4, butyrate). Optionally, in some embodiments, it is also possible to recycle the short-chain fatty acid salts or some of the short-chain fatty acid salts 134, which could still be in solution (uncrystallized) or they may have already been crystallized, back to the fermentation 110, where they may continue to elongate into medium-chain fatty acid salts. Such would be desired if we want to maximize production of the medium-chain fatty acid salts. This recycle might require some purge 135 to avoid accumulation of some minerals, but this purge can be sent to drying 140, in some embodiments, to avoid losing any of the acids in the solution. For attaining crystallization, any crystallizer unit, which would be known to those skilled in the art, would be adequate followed by a filtration or centrifugation device to separate the salts that crystallize and precipitate from concentrated liquid. The precipitated or crystallized salts are sent to a drying 140 to produce dry (less than 30% moisture content) carboxylic acid salts using a dryer, which could be, but not limited to, a fluidized-bed dryer, a flash dryer or some other convection dryer that handles wet solids at its inlet. Water 141 is also removed in drying step 140, and in some embodiments, if condensed, such water can be joined to the water 131 exiting the concentration/crystallization 130 and may be recycled 115 to the fermentation 110, or it may also be an output from the system 132.

TABLE 1

Solubility of different calcium carboxylic acid salts at 100° C. (Seidel, A. "A Compilation of Quantitative Solubility Data from Periodical Literature", $2^{nd}$ Ed., 1919)

| Calcium salt | C# | g/100 g solution |
|---|---|---|
| Acetate | C2 | 22.9 |
| Propionate | C3 | 32.6 |
| Isobutyrate | C4 | 20.7 |
| Butyrate | C4 | 13.7 |
| Isovalerate | C5 | 14.2 |
| Valerate | C5 | 8.1 |
| Caproate | C6 | 2.5 |
| Heptoate | C7 | 1.2 |
| Caprylate | C8 | 0.5 |

In some embodiments, other cations, such as potassium, might not allow crystallization. Unlike the processes where salts crystallize and precipitate, as mentioned, those salts which are not easy to crystallize, would have their concentrated broth sent directly to drying 140 to produce dry (less than 30% moisture content) carboxylic acid salts, where a dryer, which can process slurries or concentrated liquids at its inlet is used. Such dryer can be, as non-limiting examples, a rotary-drum dryer, a flash dryer, or a spray dryer. After a dry product 142 is obtained in step 140, further processing might be required. For instance, from a rotary-drum dryer, flakes are obtained, which if undesired, they would need to be broken up into a powder using a grinder, such as, but not limited to, a ball mill. On the other hand, other dryers, such as, but not limited to, a flash dryer or a spray dryer, directly produce a fine powder, which can be sent directly to packaging 150, to generate the final packaged product 151 to be marketed as a natural preservative or as a nutritional supplement.

Figure 2:
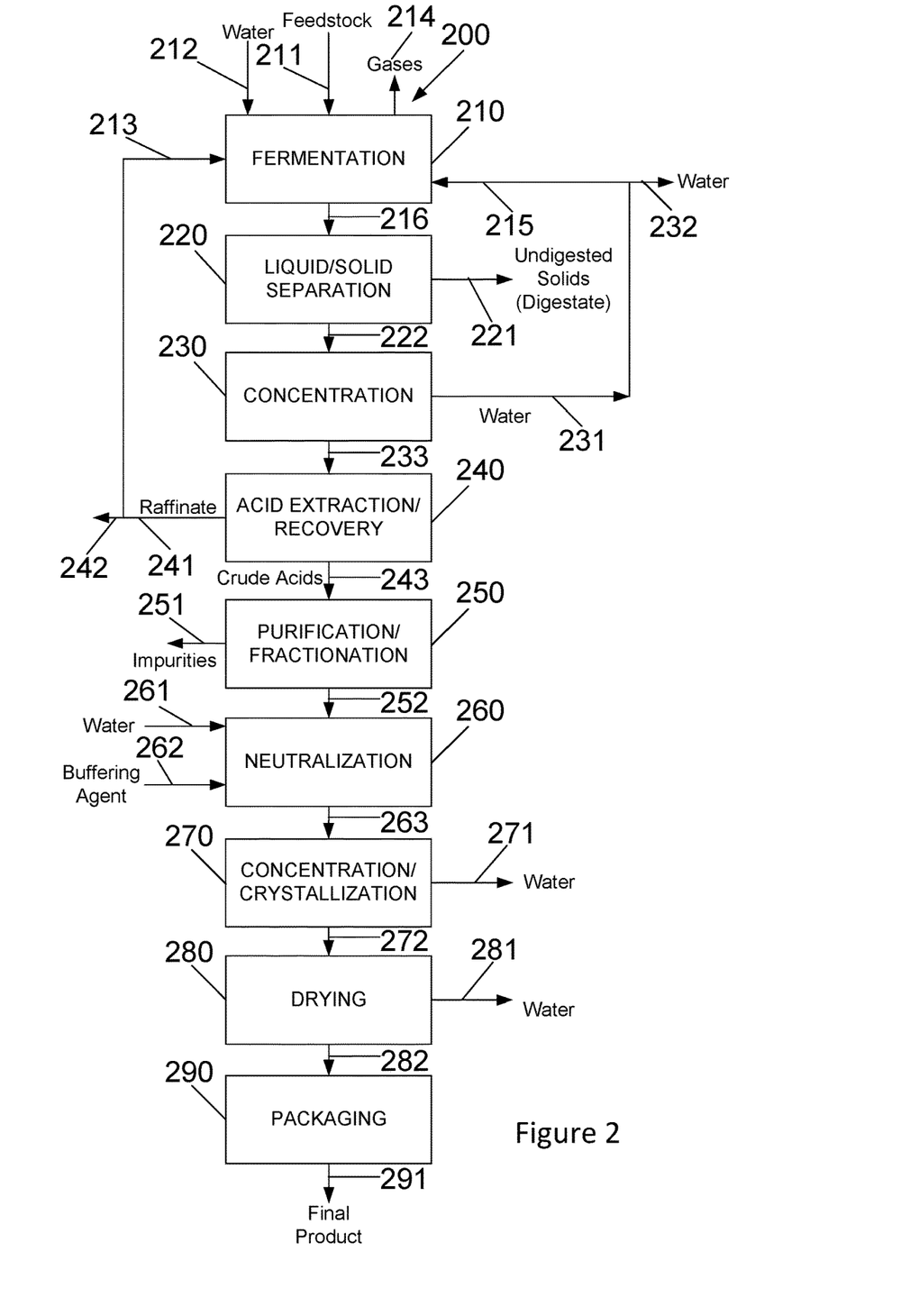
FIG. 2 shows a natural mixed-acid fermentation for producing short- and medium-chain fatty acid salts with further processing of the effluent containing these salts followed by recovery of the short- and medium-chain fatty acids from their salts for purification or fractionation, and subsequent neutralization of the acids to produce salts and thus obtain a natural dry product that may be sold as a natural preservative or as a nutritional supplement.

The above-described Process 100 directly recovers the organic salts formed in the fermentation into a dry form with some clean-up steps prior to concentration and drying. This process, however, is unable to further purify and fractionate the acids formed. Albeit, if crystallization is possible, some rough fractionation of the different salts is possible as mentioned above. However, more purification and better fractionation is only possible if the acids are recovered from the salts, so that they can be distilled. Process 200 depicted in FIG. 2 shows a process where after the mixed-acid fermentation and similarly to what occurs in Process 100, solids are removed from the fermentation effluent containing the carboxylic acid salts to clarify it and then concentrated. However, instead of continuing on to further concentration for crystallization and drying, the acids are recovered or extracted from the concentrated broth. Such recovery may be effected using various methods, such as those described in U.S. Pat. No. 10,662,447, which is incorporated here by reference in its entirety for all purposes. The crude acids are then purified and fractionated as desired using distillation, prior to once again subjecting the fractions to neutralization with alkali to convert them back into organic salts, which may be crystallized and/or dried to produce a purer and more customized natural product that can be used as preservative or nutritional supplement. For instance, pure natural butyric acid can be fractionated out of the mixed carboxylic acids, and as such butyrate products, which are quite common in the market, can be produced but unlike what is available in the market, which are petroleum-based, this product can be considered natural and clean label.

Process 200 is similar to Process 100. FIG. 2 shows Process 200 for the production of a dry product containing mixed carboxylic acid salt as in FIG. 1 with Process 100, which can be marketed as natural preservative or nutritional supplement. This dry product, however, is purer and it can be more customized as far as composition and acid profile compared to the dry product produced with Process 100. Process 200 includes feeding into mixed-acid fermentation 210, where a mixed culture of naturally occurring microorganisms produces mixed carboxylic acids or VFAs, a biodegradable feedstock 211, which can be chosen to satisfy certain characteristics, such as, but not limited to, non-GMO, organic, gluten-free, free of allergens, organic, Kosher, Halal. The feedstock 211 may be prepared in various ways as necessary, such as, by grinding, or by sorting in some cases, prior to feeding to mixed-acid fermentation 210, and it might be fed along with water 212 (if necessary when the feedstock moisture content is low to attain a solids content of <20% but preferably <10%) with a large amount of the required water also being recycled from upstream unit operations 215. Temperature and pH, which tends to drop as the mixed acids are formed, are controlled. Temperature is typically kept at around 40° C., and may be controlled with, for example and not limited to, a sludge heater or heat exchanger, where hot water or steam if heating is needed or, at times, cooling water if cooling is needed, is passed through, while the fermentation contents are pumped through such heater or exchanger. On the other hand, pH is maintained at neutral (around 6.8 to 7) by recycling raffinate 213 from the acid extraction process 240, which recycles the buffering agent and any unextracted acids. Optionally, if needed, a separate buffering agent as in Process 100, can also be added. Lower temperatures (30° C. to 40° C.) and lower pH (5 to 7) have been employed to enhance the production of medium-chain fatty acids (caproic, heptanoic and caprylic acids, C6-C8, although small quantities of larger acids, C9-C11 can be also observed) and higher temperatures (40° C. to 60° C.) and higher pH (7 to 8) are known to enhance the production of short-chain fatty acids (C2-C4, acetic, propionic, isobutyric, butyric, valeric, isovaleric acids, C2-C5) with acetic acid (C2) being the main acid produced (>70%) at temperatures above 50° C. and pH above 7.2.

The neutral pH allows for more conversion of the feedstock into mixed carboxylic acids, and feedstock conversion drops as the pH deviates from about 6.8. As a result, if, for instance, a higher amount of medium-chain fatty acids are desired, a two-stage fermentation configuration may be employed, with the pH in the first stage being kept neutral to maximize conversion, whereas the pH in the $2^{nd}$ stage is kept at a lower pH (e.g., 6 to 6.5) to maximize elongation to the medium-chain fatty acids. This operation might also be advantageous as the short-chain fatty acids (C2 and C3 mostly), which are recycled with the raffinate 213, have a chance to be elongated by microorganisms. Other ways to effect a change in the acid profile is to choose certain feedstocks or supplement the fermentation with certain feedstocks. For instance, the addition of ethanol or other reducing agents like lactate and even hydrogen, can enhance elongation towards medium-chain fatty acids (U.S. patent application Ser. No. 12/745,226, Kucek L. A. et al. Water Res. 93:163-171, 2016).

In addition to the mixed carboxylic acids, gases 214 are also produced in mixed-acid fermentation 210, which are mostly carbon dioxide and hydrogen. Methane may also be produced as a gas, but it should be avoided because this may indicate degradation of the acids as acetoclastic methanogens consume the acids to produce methane and carbon dioxide. Also, although methane is also produced from the autotrophic conversion of carbon dioxide and hydrogen, hydrogen is used by certain microorganisms for the elongation of short-chain fatty acids to medium-chain fatty acids, so if such elongation is desired, this is another reason to avoid methane production. As a result, methane production should be inhibited. Methane inhibition may be effected through different methods, such as controlling conditions, such as lowering pH, or by the addition of certain methane inhibitors such as, but not limited to, long-chain fatty acids (Hanaki K. et al., Biotechnol Bioeng 23(7): 1591-1610, 1981), methane analogues (Thiel P., Water Res 3(3): 215-223, 1969), ionophores (Guan H. et al, J Anim Sci 84(7): 1896-1906) and others (Hristov A. et al, Proc Natl Acad Sci U.S.A. 112(34): 10663-10668, 2015), or by the combination of the methods and inhibitors thereof From the mixed-acid fermentation 210, an effluent 216 containing the produced organic salts of the mixed carboxylic acids (also known as carboxylate salts), water and any undigested solids, which would include the microorganisms, is generated. A liquid/solid separation step, 220, may be required to remove the undigested suspended solids or digestate 221, which comprises of the parts of the solid feedstock that are hard to digest or it may also comprise of microorganisms. Such liquid/solid separation process can be, but not limited to, a centrifuge (e.g., decanter centrifuge, basket centrifuge), a filtration system (e.g., plate-and-frame filter press, rotary-drum filter, belt filter press), a membrane filtration system (e.g., microfiltration, ultrafiltration, nanofiltration), high-speed centrifugation, or combinations thereof. A flocculation chemical, a coagulation chemical or combination thereof may be added in this step as necessary for the proper functioning of the liquid/solid separation process, and filter aid (e.g., diatomaceous earth) may also be employed, as necessary. The resulting digestate 221 may be further washed to recover as much as the organic acid salts still present and then the wash water containing the recovered organic acid salts may be sent back to the fermentation 210. The digestate 221 may be disposed of or it may be sent to composting to be land applied. Yet part of the digestate 221 may be recycled to the fermentation 210 for further conversion. The filtrate effluent from the filtration or the supernatant effluent from the centrifugation may be further cleaned up or clarified to further remove suspended solids. Such cleaning or clarification may be important to improve the quality of the effluent. Such cleaning or clarification may be done using microfiltration, ultrafiltration, nanofiltration membranes or combinations thereof. Yet another method for removal of suspended solids to clean up and clarify the effluent may be high-speed centrifugation (above 10,000 RPM). The retentate from the membrane clarification containing the suspended solids or the centrifuged suspended solids from the high-speed centrifugation may be recycled to the fermentation for further conversion. The resulting permeate from the membrane clarification or the supernatant from the high-speed centrifugation 222 is then sent to concentration 230.

Concentration 230 has the objective of removing water 231 from the clarified effluent to increase the concentration of the organic salts. Such concentration may occur by reverse osmosis (RO) with membranes, by evaporation or by combinations thereof. Typically, RO is used first when the concentration is low followed by evaporation as the concentration gets to a point where the required RO pressure would be too large. This strategy of using RO followed by evaporation can minimize operating costs, nonetheless, in some embodiments, both RO and evaporation may be employed alone. The evaporator can be of any type, such as, but not limited to, a simple evaporator, multiple-effect evaporator, mechanical vapor-recompression evaporator and thermocompression evaporator. pH may be increased in this step by adding alkali, for instance sodium, potassium, ammonium, calcium or magnesium hydroxide or carbonate or combinations thereof. The purpose of increasing the pH is avoiding the loss of the organic acids both during the RO step and the evaporation. In the RO step, undissociated acids may go through the membrane easier than salts, which surround themselves with water molecules. During the evaporation, on the other hand, making sure that all the acids are indeed in the salt form rather than undissociated is also important to avoid the acids from volatilizing. Typically, a pH above 8.5 is enough to avoid acid losses in RO and evaporation.

From RO, the permeate that goes through the membrane is very pure potable water. Also, the evaporators would produce as outputs the concentrated liquid 233 and the water removed would also be recovered as condensate. The water 231 obtained from this concentration step either in RO, evaporation or both may be recycled 215 to fermentation 210, or if the feedstock moisture content is high, then excess water 232 may be an output from the system. The water should be good quality either RO-quality or distilled water in the condensate from evaporation. Now, at high pH, ammonia, which, if not added as alkali or buffer, is also produced from the degradation of proteins in the mixed-acid fermentation 110, will be removed during RO but mostly during evaporation. Some of the ammonia will end up in the RO water, but a more significant amount will end up in the condensate from the evaporation. The ammonia will need to be removed to be able to outfall excess water 232. Even if the water is to be recycled 215 to fermentation 210, it also requires the removal of some ammonia to avoid ammonia accumulation. Ammonia removal can take place by many methods, such as, but not limited to, ion exchange, hollow fiber membranes under vacuum, and air or steam stripping. The removed ammonia may be recovered with sulfuric acid as liquid ammonium sulfate, which can be sold as fertilizer.

The concentrated broth obtained from the concentration step 230, could have some precipitation in the form of some minerals, such as phosphates and struvite, which fall out of solution due to the removal of ammonia and other electrolyte chemistry alterations occurring during concentration. It is recommended to implement filtration, such as bag filters, filter presses, or even membrane microfiltration, ultrafiltration or nanofiltration to remove such precipitated minerals. The concentrated filtrate or broth 233 is then sent to acid extraction and recovery 240 where methods as described in U.S. Pat. No. 10,662,447 may be employed to extract acids from the salts in the concentrated broth 233. The salts are acidified, and then the resulting acids are extracted using methods, which do not use extraneous solvents, thus maintaining a natural and sustainable process. For instance, a preferred embodiment, as described in U.S. Pat. No. 10,662,447, employs carbon dioxide, which is produced in the fermentation, as the extractant. As mentioned, the extraction raffinate 241, which contains the cations of the salts, unextracted carboxylic acid salts, and other components, such as carbonates (in the case where carbon dioxide is the acidification agent), is recycled 213 to fermentation 210 to act as the buffering agent. Some of this raffinate may also be purged 242 to avoid accumulation of minerals, such as the cations of the organic salts, as more of these minerals enter the system with the feedstock.

The extracted acids are separated from the solvent (e.g., carbon dioxide) and these crude mixed carboxylic acids 243 are then sent to purification/fractionation where they are purified with, for example, distillation and impurities 251 may be recovered and removed. Such impurities may be high-boiling point (e.g., long-chain fatty acids or oils) or low-boiling point (e.g., water). Then pure mixed carboxylic acids can be fractionated, also using distillation, into, for instance, short-chain and medium-chain fatty acids, or they can even be fractionated into individual acids, such as butyric acid. These fractions of pure mixed or individual carboxylic acids 252 are now sent to neutralization 260.

In the neutralization step 260, the pure mixed or individual acid fractions 252 are converted back into salts by adding an alkali as buffering agent 262. Such can be, but are not limited to, sodium, potassium, ammonium, calcium or magnesium hydroxide or carbonate or combinations thereof. In some embodiments, water 261 may optionally be added to allow better mixing and have better control during the neutralization process. The neutralized acids 263, which are now the organic salts of those acids, are then sent to concentration 270 for water removal.

In some embodiments, crystallization occurs during concentration 270 when the salts fall or precipitate out of solution as further concentration takes place, which means water 271 continues to be removed during the crystallization process. Such phenomenon has been observed with calcium salts, for instance, where the salts of the medium-chain fatty acids (C6 through C8) precipitate first, followed by the short-chain fatty acid salts (C2 through C5). As the salts are precipitated, they may be filtered out or centrifuged out. Because each salt will precipitate when different concentrations are reached depending on their own water solubility at a given temperature (See Table 1, the solubilities of calcium carboxylic acid salts at 100° C.), and the crystallized carboxylic acid salts may be recovered as they form (e.g., through filtration or centrifugation), the crystallization process is able to selectively separate, up to a certain degree, the different carboxylic acid salts present, thus it may produce salt fractions with different carboxylic acid profiles. For instance, in some embodiments, a fraction of the salts may have a salt profile with a higher concentration of medium-chain fatty acid salts (C6 through C8) and another fraction with a higher concentration of short-chain fatty acid salts (C2 through C5), yet another embodiment might be directed to concentrate a particular salt (e.g., C4, butyrate). For attaining crystallization, any crystallizer unit, which would be known to those skilled in the art, would be adequate followed by a filtration or centrifugation device to separate the salts that crystallize and precipitate from concentrated liquid. The precipitated or crystallized salts are sent to drying 280 to produce dry (less than 30% moisture content) carboxylic acid salts using a dryer, which could be, but not limited to, a fluidized-bed dryer, a flash dryer or some other convection dryer that handles wet solids at its inlet. Water 281 is also removed in drying step 280, and in some embodiments, if condensed, such water can be joined to the water 271 exiting the concentration/crystallization 270 and the water 231 exiting concentration 230 and it may be recycled 215 to the fermentation 210, or it may also be an output from the system 232.

In some embodiments, other cations, such as potassium, might not allow for crystallization. Unlike the processes where salts crystallize and precipitate, as mentioned, those salts which are not easy to crystallize, would have their concentrated broth sent directly to drying 280 to produce dry (less than 30% moisture content) carboxylic acid salts, where a dryer, which can process slurries or concentrated liquids at its inlet is used. Such dryer can be, as non-limiting examples, a rotary-drum dryer, a flash dryer, or a spray dryer. After a dry product 282 is obtained in step 280, further processing might be required. For instance, from a rotary-drum dryer, flakes are obtained, which if undesired, they would need to be broken up into a powder using a grinder, such as, but not limited to, a ball mill. On the other hand, other dryers, such as, but not limited to, a flash dryer or a spray dryer, directly produce a fine powder, which can be sent directly to packaging, 290, to generate the final packaged product 291 to be marketed as a natural preservative or as a nutritional supplement.

EXAMPLE 1. An example of mixed carboxylic acid profile produced in mixed-acid fermentation can be observed in Table 2. The example feedstock used to produce the mixed carboxylic acid profile in Table 2 is a combination of oats, vegetable protein and sugarcane molasses at a pH of 6.5 at 40° C. with a mixture of sodium and potassium carbonate as buffering agents.

TABLE 2

Acid Profile from Mixed Acid Fermentation of Oats/Vegetable protein/Molasses

| Acid | Other Name | C# | % wt |
|---|---|---|---|
| Acetic | Ethanoic | C2 | 34.1% |
| Propionic | Propanoic | C3 | 9.0% |
| Isobutyric | 2-methylpropanoic | C4 | 1.5% |
| Butyric | Butanoic | C4 | 19.4% |
| Isovaleric | 3-methylbutanoic | C5 | 2.9% |
| Valeric | Pentanoic | C5 | 7.1% |

TABLE 2-continued

Acid Profile from Mixed Acid Fermentation of Oats/Vegetable protein/Molasses

| Acid | Other Name | C# | % wt |
|---|---|---|---|
| Caproic | Hexanoic | C6 | 17.9% |
| Enanthic | Heptanoic | C7 | 5.6% |
| Caprylic | Octanoic | C8 | 2.4% |
| Others | | C9-C11 | <0.01% |
| | | TOTAL | 100.0% |

Advantages. Embodiments of the disclosure may advantageously provide a natural method of producing carboxylic acid or VFA salts, which presently are produced mostly from petroleum or natural gas. Embodiments disclosed offer advantages over other methods of producing natural preservatives and nutritional supplements in that they allow the use of a wide variety of natural feedstocks with desired characteristics such as, but not limited to, GMO-free, organic, Kosher, Halal, gluten-free, free of allergens, clean label and natural. Embodiments also offer advantages over other methods of producing natural preservatives and nutritional supplements in that they allow the fractionation of the different carboxylic acid salts to produce a desired composition or profile of such salts. Embodiments also offer advantages in that the extraction and recovery of the carboxylic acids from the salts allows the purification of the acids, thus producing purer salts than what other methods for producing natural preservatives and nutritional supplements can produce.

The disclosures of all patents, patent applications, and publications cited herein are hereby incorporated by reference, to the extent they provide some, procedural or other details supplementary to those set forth herein.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The inclusion or discussion of a reference is not an admission that it is prior art to the present invention, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

What is claimed is:

1. A process for producing products containing carboxylic acid salts from a biodegradable feedstock, the process comprising:
   fermenting the biodegradable feedstock using a natural consortia of microorganisms to produce a first product stream comprising the carboxylic acid salts, suspended solids, and water, wherein the carboxylic acid salts comprise C2-C5 short-chain fatty acid salts, C6-C9 medium-chain fatty acid salts, or a combination of C2-C5 short-chain fatty acid salts and C6-C9 medium-chain fatty acid salts;
   removing the suspended solids from the first product stream to produce a second product stream comprising the carboxylic acid salts and water;
   concentrating the second product stream by removing a portion of the water from the second product stream to produce a third product stream and water, wherein the third product stream is sufficiently concentrated to cause crystallization of at least a portion of the carboxylic acid salts contained therein;
   recovering the crystallized carboxylic acid salts from the solution as they form, wherein the salts still remaining in solution after the separation of the crystallized carboxylic acid salts form a fourth stream comprising fractionated carboxylic acid salts;
   recycling at least a portion of the fourth product stream to the fermenting step; and
   drying at least a portion of the recovered crystallized carboxylic acid salts to remove water and produce a fifth product stream comprising dry carboxylic acid salts.

2. The process of claim 1, wherein the fermentation of the biodegradable feedstock comprises anaerobic fermentation with a mixed culture of natural microorganisms in a fermentation vessel or system of vessels.

3. The process of claim 1, wherein the fermenting is conducted at a pH between 5 and 8.

4. The process of claim 1, wherein the fermenting is conducted at a pH between 6 and 7.

5. The process of claim 1, wherein the fermenting is conducted at a temperature between 30° C. and 60° C.

6. The process of claim 1, wherein the fermenting is conducted at a temperature between 35° C. and 45° C.

7. The process of claim 1, wherein methane production during the fermenting is inhibited.

8. The process of claim 1, wherein the removing suspended solids from the first product stream comprises filtration, centrifugation, membrane filtration, high-speed centrifugation, or a combination of any two or more thereof.

9. The process of claim 8, wherein the removing suspended solids from the first product stream after filtration or centrifugation comprises clarifying by membrane filtration, high-speed centrifugation, or a combination of any two or more thereof.

10. The process of claim 1, wherein the concentrating the second product stream comprises reverse osmosis, evaporation, or a combination of any two or more thereof.

11. The process of claim 1, wherein the water produced by concentrating the second product stream is recycled to the fermenting step.

12. The process of claim 1, wherein at least one fraction of the fractionated carboxylic acid salts is recycled to the fermenting step.

13. The process of claim 1, wherein drying the crystallized carboxylic acids salts comprises using at least one of a fluidized-bed dryer, a flash dryer, other convection dryer, and combinations thereof.

14. The process of claim 1, wherein the fifth product stream is further ground or milled to produce a sixth product stream comprising fine powder of the dry carboxylic acid salts.

15. The method of claim 1, wherein the carboxylic acid salts contained in the portion of fourth product stream recycled to the fermenting step are C2-C5 short-chain fatty acid salts.

16. A process for producing products containing carboxylic acid salts from a biodegradable feedstock, the process comprising:

fermenting the biodegradable feedstock using a natural consortia of microorganisms to produce a first product stream comprising the carboxylic acid salts, suspended solids, and water, wherein the carboxylic acid salts comprise C2-C5 short-chain fatty acid salts, C6-C9 medium-chain fatty acid salts, or a combination of C2-C5 short-chain fatty acid salts and C6-C9 medium-chain fatty acid salts;

removing the suspended solids from the first product stream to produce a second product stream comprising the carboxylic acid salts and water;

concentrating the second product stream by removing a portion of the water from the second product stream to produce a third product stream and water, wherein the third product stream is sufficiently concentrated to cause crystallization of at least a portion of the carboxylic acid salts contained therein;

recovering the crystallized carboxylic acid salts from the solution as they form, wherein the salts still remaining in solution after the separation of the crystallized carboxylic acid salts form a fourth stream comprising fractionated carboxylic acid salts;

recycling at least a portion of at least one of the fourth product stream and the recovered crystallized carboxylic acid salts to the fermenting step; and drying at least a portion of the recovered crystallized carboxylic acid salts to remove water and produce a fifth product stream comprising dry carboxylic acid salts.

17. The process of claim 1, wherein the carboxylic acid salts produced by the fermentation comprise salts of ethanoic, propionic, isobutyric, butyric, isovaleric, valeric acids, caproic, enanthic, or caprylic acids.

* * * * *